(12) United States Patent
Barker et al.

(10) Patent No.: US 11,598,708 B2
(45) Date of Patent: Mar. 7, 2023

(54) DETERMINE PARTICLE SIZE DISTRIBUTION BY SIZE EXCLUSION CHROMATOGRAPHY

(71) Applicant: Malvern Panalytical Limited, Malvern (GB)

(72) Inventors: Oksana Iryna Barker, Malvern (GB); Oluseyi Latunde-Dada, Malvern (GB); Markos Trikeriotis, Malvern (GB); David Robert Barker, Malvern (GB)

(73) Assignee: Malvern Panalytical Limited, Malvern (GB)

( * ) Notice: Subject to any disclaimer, the term of this patent is extended or adjusted under 35 U.S.C. 154(b) by 205 days.

(21) Appl. No.: 16/771,592

(22) PCT Filed: Dec. 11, 2018

(86) PCT No.: PCT/GB2018/053582
§ 371 (c)(1),
(2) Date: Jun. 10, 2020

(87) PCT Pub. No.: WO2019/116015
PCT Pub. Date: Jun. 20, 2019

(65) Prior Publication Data
US 2020/0300743 A1    Sep. 24, 2020

(30) Foreign Application Priority Data

Dec. 11, 2017  (GB) .................................... 1720574
Feb. 9, 2018   (GB) .................................... 1802169

(51) Int. Cl.
*G01N 15/02*   (2006.01)
*B01D 15/38*   (2006.01)
(Continued)

(52) U.S. Cl.
CPC ..... *G01N 15/0205* (2013.01); *B01D 15/3809* (2013.01); *B01J 47/026* (2013.01);
(Continued)

(58) Field of Classification Search
CPC .... B01D 15/34; B01D 15/3809; B01J 47/026; C07K 1/18; G01N 15/02; G01N 15/0205; G01N 2015/0693; G01N 30/02
(Continued)

(56) References Cited

U.S. PATENT DOCUMENTS 5,269,937 A       12/1993  Dollinger et al.
2003/0041969 A1*  3/2003   Schneider .............. G01N 15/06
                                                         156/345.24
(Continued)

FOREIGN PATENT DOCUMENTS

WO    2013/021185 A1    2/2013

OTHER PUBLICATIONS

International Search Report and Written Opinion dated Mar. 15, 2019, directed to PCT Application No. PCT/GB2018/053582; 14 pages.
(Continued)

*Primary Examiner* — Tri T Ton
(74) *Attorney, Agent, or Firm* — Morrison & Foerster LLP

(57) ABSTRACT

A method and an apparatus for characterising a sample comprising particles is disclosed. The method comprises performing a first measurement on the sample using a first particle characterisation technique; flowing the sample from the first particle characterisation technique to a particle separating device; separating the sample with the particle separating device; and performing a second measurement on the separated sample. The apparatus is configured to perform the method, and comprises a measurement system for per-
(Continued)

forming measurements according to a first particle characterisation technique and a particle separating device for separating samples comprising particles.

18 Claims, 14 Drawing Sheets

(51) Int. Cl.
*B01J 47/026* (2017.01)
*C07K 1/18* (2006.01)
*G01N 30/02* (2006.01)
*G01N 15/06* (2006.01)

(52) U.S. Cl.
CPC ............... *C07K 1/18* (2013.01); *G01N 30/02* (2013.01); *G01N 2015/0693* (2013.01)

(58) Field of Classification Search
USPC .... 356/335–343, 237.1–237.6, 239.1–239.8, 356/243.2
See application file for complete search history.

(56) References Cited

U.S. PATENT DOCUMENTS

| | | |
|---|---|---|
| 2012/0091063 A1 | 4/2012 | Bangtsson et al. |
| 2016/0033470 A1 | 2/2016 | Reed |
| 2016/0320381 A1* | 11/2016 | Holmes ................ G01N 35/026 |
| 2017/0212029 A1* | 7/2017 | Scharmach ............ G01N 21/53 |

OTHER PUBLICATIONS

Notice of Reasons for Refusal dated Nov. 17, 2022, directed to JP 2020-531738; 6 pages.

* cited by examiner

DETERMINE PARTICLE SIZE DISTRIBUTION BY SIZE EXCLUSION CHROMATOGRAPHY

CROSS-REFERENCE TO RELATED APPLICATIONS

This application is a national stage application under 35 USC 371 of International Application No. PCT/GB2018/053582, filed Dec. 11, 2018, which claims the priority of United Kingdom Application Nos. 1720574.1 filed Dec. 11, 2017 and 1802169.1 filed Feb. 9, 2018, the entire contents of each of which are incorporated herein by reference.

FIELD OF THE DISCLOSURE

The invention relates to a method and apparatus for determining particle characteristics.

BACKGROUND OF THE DISCLOSURE

Novel biopharmaceuticals are typically analysed using aggregation profiling. Size exclusion chromatography (SEC) is often used to separate a sample based on particle size or mass. However, the sample output from the SEC column may not be a true representation of the sample. Larger particles or aggregations of particles may be prevented from traveling through the SEC column, and so will be missing from the particle size/mass distribution analysis. To correct for this problem, the SEC measurements may have to be validated by another technique, typically analytical ultracentrifugation (AUC). AUC is a difficult, expensive, and time consuming technique.

Investigation of aggregation characteristics of particles may require a large range of particle sizes to be investigated. Previously, multiple analyses have been carried out using different instruments with different measurement modalities in order to provide coverage of a large range of particle sizes. This may be time consuming and inconvenient.

SUMMARY OF THE DISCLOSURE

In accordance with a first aspect of the invention there is provided a method of characterising a sample comprising particles, the method comprising: performing a first measurement on the sample using a first particle characterisation technique; flowing the sample from the first particle characterisation technique to a particle separating device; separating the sample with the particle separating device; and performing a second measurement on the separated sample.

Performing a first measurement with the first measurement technique before separating the sample with the particle separating device yields a representation of the true sample composition of the actual sample which is to be passed through the particle separating device. This may be used to determine if any sample is lost during separation, for example if larger particles are prevented from passing through the particle separating device. For example, the first measurement may be compared to the second measurement, and/or to an additional measurement, to determine if any particles of the sample have been lost. For example a particle size or particle mass distribution determined from the first measurement may be compared to a particle size or particle mass distribution determined from the second measurement or an additional measurement.

By determining whether a true representation of the sample has been separated by the particle separating device, the need for expensive validation techniques such as AUC may be avoided.

The second measurement may be performed by the particle separating device itself, for example the particle separating device may comprise a sample measurement instrument for measuring the separated sample. Alternatively or additionally, the second measurement may be performed by a separate instrument configured to measure the sample output from the particle separating device.

The second measurement may determine a property of the separated sample as a function of time, for example providing an indication of a variation of a particle characteristic of the particles in the separated sample over time. The particle separating device may cause particles to be separated in time based on the particle characteristic (for example, causing particles with different sizes or different degrees of adsorption interaction with an adsorbent to have a different elution time). The second measurement may use the first particle characterisation technique, or an alternative particle characterisation technique. The second measurement may use the same instrument used for the first measurement.

References to flowing the sample to or from the first particle characterisation technique should be understood to mean flowing the sample to or from a position at which a measurement according to the first particle characterisation technique may be performed.

Performing a first measurement using a first particle characterisation technique may comprise performing a plurality of first measurements, each of the plurality of first measurements performed using a respective particle characterisation technique.

The particle separating device may be a fractionating device. The particle separating device may comprise a chromatography column, for example a size exclusion chromatography column. The particle separation device may perform any technique that may be used to separate a sample mixture into more than one distinct population, such as:

size exclusion chromatography (for example, gel permeation chromatography or gel filtration chromatography);

field flow fractionation and associated variants such asymmetric flow field flow fractionation (AF4);

other liquid chromatography columns (both analytical and preparative) including: affinity, ion exchange, hydrophobic interaction, monolithic, and micro pillar array columns; hydrodynamic chromatography;

deterministic lateral displacement (DLD) devices;

packed bead beds such as silica; and filters including using one or more size cut-off filters.

The second measurement may be or comprise a photometry measurement, for example a UV photometry measurement.

The method may further comprise determining a particle characteristic distribution of the sample, for example a particle mass distribution or particle size distribution.

In some embodiments, the method may further comprise flowing the sample from the separator device back to the first particle characterisation technique. A further measurement using the first particle characterisation technique may then be performed, allowing determination of whether any particles have been lost. The further measurement may be an ensemble measurement on the whole sample, or may be a time dependent measurement on the separated sample.

Some embodiments may comprise performing an additional measurement on the sample before and/or after separating the sample with the particle separating device. Performing the additional measurement may comprise performing an additional measurement on the sample using the first particle characterisation technique, for example by flowing the sample from the particle separating device to the first measurement technique as described above. Alternatively or additionally, performing the additional measurement on the sample may comprise performing an additional measurement on the sample using a second particle characterisation technique, different from the first particle characterisation technique.

The method may further comprise comparing the first measurement and the second measurement to determine if all particles of the sample have passed through the separating device. In an embodiment, comparing the first measurement and second measurement comprises determining if the second measurement matches the first measurement. If the second measurement does match the first measurement, determining that all particles of the sample have passed through the separating device; and if the second measurement does not match the first measurement, determining that not all of the particles of the sample have passed through the separating device.

In some embodiments, the method may further comprise comparing the first measurement and the additional measurement to determine if all particles of the sample have passed through the separating device. In particular, comparing the first measurement and additional measurement may comprise: determining if the additional measurement matches the first measurement. If the additional measurement does match the first measurement, the method may comprise determining that all particles of the sample have passed through the separating device. If the additional measurement does not match the first measurement, the method may comprise determining that not all of the particles of the sample have passed through the separating device.

In some embodiments, determining if the second measurement and/or additional measurement matches the first measurement comprises determining if a particle size extracted from the second measurement and/or additional measurement matches a particle size extracted from the first measurement. The particle size may be an average particle size. The particle size may be an average hydrodynamic radius.

Alternatively or additionally, determining if the second measurement and/or additional measurement matches the first measurement may comprise determining if a particle concentration extracted from the second measurement and/or additional measurement matches a particle concentration extracted from the first measurement. In yet another embodiment, determining if the second measurement and/or additional measurement matches the first measurement may comprise determining if a particle size distribution extracted from the second measurement and/or additional measurement matches a particle size distribution extracted from the first measurement.

Extracting a particle size distribution may comprise performing a non-negative least squares (NNLS) fit.

In some embodiments, flowing the sample from the first particle characterisation technique to the particle separating device may comprise operating a valve (or valves) to direct the sample from the first particle characterisation technique to the particle separating device. For example, flowing the sample from the first particle characterisation technique to the particle separating device may comprise operating a valve to connect an output of the first particle characterisation technique to an input of the particle separating device. The valve may be a rheodyne switch valve.

In embodiments wherein the sample is flowed from the particle separating device back to the first particle characterisation technique, flowing the sample from the particle separating device to the first particle characterisation technique may comprise operating a valve to direct the sample from the particle separating device to the first particle characterisation technique, and may comprise operating the valve to connect an output of the particle separating device to an input of the first particle characterisation technique.

In some embodiments, the first particle characterisation and/or second particle characterisation technique is an ensemble particle characterisation technique. The particle characterisation technique may be selected from the group comprising: UV spectroscopy, dynamic light scattering, static light scattering, Taylor dispersion analysis, and UV photometry.

Where the particle characterisation technique is or comprises Taylor dispersion analysis (TDA), the output of the particle characterisation measurement is or comprises a concentration distribution (Taylorgram).

Determining if the second measurement and/or additional measurement matches the first measurement may comprise fitting the Taylorgram with one or more parametric model functions to extract a particle size. The one or more parametric models may be or comprise a time-dependent Gaussian function.

Alternatively or additionally, determining if the second measurement and/or additional measurement matches the first measurement may comprise performing a NNLS fit to the Taylorgram with one or more parametric model functions to extract a particle size distribution. The one or more parametric models may be or comprise a time-dependent Gaussian function.

The method may comprise fitting one or more parametric model functions to a result from the first measurement and/or a result from the second measurement. The parametric model functions may comprise time-dependent Gaussian functions.

The method may comprise performing a quantitative analysis of the proportions of the sample in the following categories:
  i) monomer, corresponding with the size of relative molecular weight of a particle of interest;
  ii) particles with lower size or molecular weight than the monomer (this category may be referred to as LMW);
  iii) oligomers of the monomer, or particles with size or molecular weight higher than the monomer, up to but not including a particle size or molecular weight that is excluded from the second measurement (this category may be referred to as HMW or aggregates); and
  iv) large aggregates, comprising particles that are large enough to be excluded from the second measurement (this category may be referred to as VHMW).

In accordance with a second aspect of the invention there is provided a particle characterisation platform comprising: a measurement system for performing measurements according to a first particle characterisation technique; and a particle separating device for separating samples comprising particles; wherein the particle characterisation platform is configured to perform the method of any of any embodiment of the first aspect.

In some embodiments, the particle separating device may comprise a chromatography column, for example a size exclusion chromatography column.

In some embodiments, the measurement system may be further configured to perform measurements according to a second particle characterisation technique.

The particle characterisation platform may be configured to flow a sample to the measurement system to perform the first measurement, then to the particle separating device to separate the sample, and then back to the measurement system to perform the second measurement.

The measurement system may be a first measurement system, and the particle characterisation instrument may comprise a second measurement system. The particle characterisation platform may be configured to flow a sample to the first measurement system to perform the first measurement, then to the particle separating device to separate the sample, and then to the second measurement system to perform the second measurement.

The first measurement may comprise UV photometry and static light scattering. The second measurement may comprise UV photometry and static light scattering.

The instrument may be configured to provide a quantitative analysis of the proportions of the sample in the following categories:
i) monomer, corresponding with the size of relative molecular weight of a particle of interest;
ii) particles with lower size or molecular weight than the monomer (this category may be referred to as LMW);
ii) oligomers of the monomer, or particles with size or molecular weight higher than the monomer, up to but not including a particle size or molecular weight that is excluded from the second measurement (this category may be referred to as HMW or aggregates); and
v) large aggregates, comprising particles that are large enough to be excluded from the second measurement (this category may be referred to as VHMW).

BRIEF DESCRIPTION OF THE FIGURES

The invention is described in further detail below, by way of example, and with reference to the accompanying drawings, in which.

DETAILED DESCRIPTION OF THE DISCLOSURE

Figure 1:
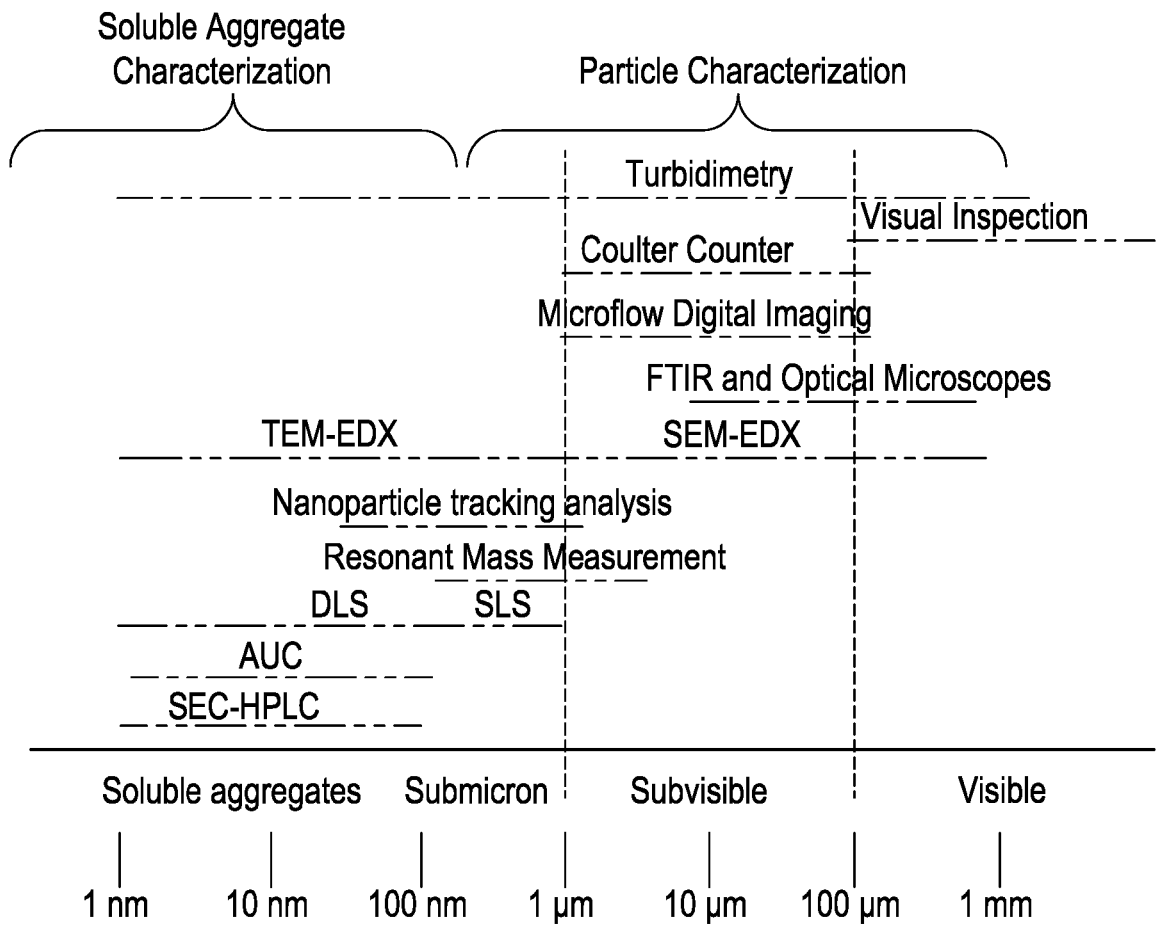
FIG. 1 illustrates the applicable particle size range for a number of measurement techniques.

Aggregation studies need to consider both monomer fragments, which may be very small, and aggregated particles, including very large aggregated particles. Protein monomers may be a few nanometers in diameter, and protein fragments even smaller than that. Aggregates may form visible particles that may be as large as 100 microns (or even larger). As illustrated in FIG. 1, SEC-HPLC (size exclusion/high performance liquid chromatography) can be used to investigate particles at the smaller end of the range for aggregation studies, but alternative measurement techniques are required to investigate larger aggregates, such as microflow digital imaging, or light scattering (dynamic or static).

Previous workflows for investigating aggregation may therefore include multiple instruments, with different portions of a sample being provided to different instruments that perform a range of different measurements. For example, SEC-HPLC may be used to investigate protein fragments, monomers and protein oligomers. A light scattering technique such as DLS may be used to extend the size of particles investigated to include larger particles. Imaging techniques may be used to investigate very large particles.

Using multiple measurement techniques in this way is time consuming. Sample preparation must be undertaken separately for each instrument, and the cumulative run time for each measurement may be significant, limiting the throughput of this sort of investigation. In addition, the results from the different measurement techniques have to be processed, combined and synthesised, often manually, in order to provide the results of the investigation into aggregation. Different types of analysis are carried out on different portions of sample, which reduces consistency and consumes relatively large quantities of the sample. Embodiments of the present disclosure may address at least some of these problems.

Figure 2:
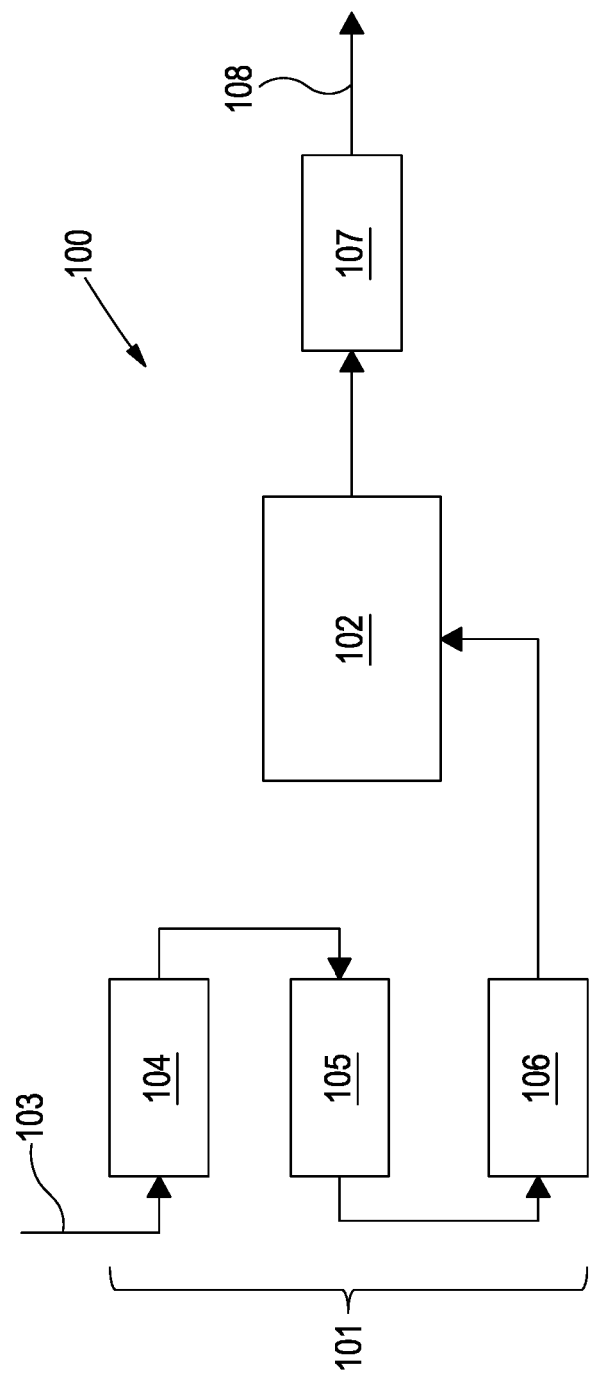
FIG. 2 is a schematic representation of a particle characterisation platform.

FIG. 2 shows a schematic representation of a particle characterisation platform 100 according to the present disclosure. Platform 100 comprises a plurality of first measurement systems 101, each configured to perform a first particle characterisation technique; and a particle separating device 102. Connections, e.g. tubing, allow a sample to flow between each of the plurality of first measurement systems 101, and then to the particle separating device 102.

In the illustrated example, the plurality of first measurement systems 101 comprise a dynamic light scattering (DLS) system 104 for performing DLS measurements on a sample; a Taylor dispersion analysis (TDA) system 105 for performing TDA measurements on the sample; and an ultraviolet (UV) photometer 106 for performing UV spectrometry measurements on the sample (e.g. UV absorption at one or more wavelength). In some embodiments, there may be a single first measurement system (e.g. one of those mentioned above), rather than a plurality of different measurement systems.

In use, a sample is flowed from an input 103 to first measurement system(s), in this example to the DLS system 104. The sample may be pumped to the input 103 by a pump (not shown in FIG. 2). The pump may provide sufficient pressure to flow the sample fully around platform 100. The DLS system 104 performs a DLS measurement on the sample. Information on the particle size distribution and hence on any aggregation of particles in the sample may be determined from the DLS measurement.

The sample is then flowed into TDA system 105, which performs a TDA measurement on the sample. Information on least one of: particle size, diffusion characteristics, the relative concentrations of different components, and aggregation (particularly of any larger aggregates in the sample), may be determined from the TDA measurement.

The sampled is then flowed into the UV photometer 106, which performs a UV photometry measurement on the sample, for example at 280 nm. Information on the total particle/protein concentration of the sample, for example, may be determined from the UV measurement.

Following the UV measurement, the entire sample which has been measured by the first measurement system(s) 101 is flowed into particle separating device 102. Particle separating device 102 separates the sample based on a particle characteristic, such as particle size. For example, larger particles may be able to pass through the particle separating device 102 at a different rate (e.g. faster) than smaller particles, and so the time at which a particle elutes from the separating device 102 may be determined by its size. The particle separating device 102 further comprises a sample measuring instrument, such as a UV photometer, which provides an indication of the concentration of particles eluting as a function of time. From this, the relative proportions of different particles sizes in the sample can be determined, for example identifying the amount of monomers, dimers, trimers, and larger aggregates in the sample (with the concentration corresponding with areas of each peak of a concentration vs time curve and the elution time of each peak corresponding with the particle size).

In the illustrated example, the particle separating device 102 comprises a size exclusion chromatography (SEC) column. Certain particles in the sample may be too large to pass through the SEC column at all. Thus an aggregation measurement performed on the separated sample (after elution, as in conventional systems) may not indicate the presence of larger aggregates, which may have been trapped by the SEC column.

In the present invention, however, the measurement from the particle separating device 102 (e.g. SEC instrument) is not taken in isolation. The first measurements acquired from the first measurement system(s) 101 provide information about the particle distribution of exactly the same sample as that fed into the particle separating device 102 (and the measurement is performed sequentially with minimal time delay, e.g. less than 5 minutes delay). Any aggregates that did not pass through the particle separating device 102 may be identifiable in the first measurements, but will not be identifiable in the measurement on the separated sample. Thus by comparing the first measurements to the measurement on the separated sample, it may be determined whether any component of the sample has been lost or retained, allowing identification of the true sample composition.

In the illustrated example, after passing through the particle separating device 102, the sample is flowed to an optional additional measurement system 107. The additional measurement system 107 performs an additional measurement on the sample. The additional measurement may then be compared to one or more of the first measurements, to further confirm whether the full sample has passed through the particle separating device 102. In particular, the additional measurement system 107 may use the same particle characterisation technique as one (or more) of the first measurement systems 101, allowing a direct comparison of the additional measurement to the matching first measurement. For example, the additional measurement system 107 may be a UV photometer, similar (of configured identically) to UV photometer 106. The UV photometers may provide an indication of the total protein concentration in the sample. Some proteins (or aggregations thereof) in particular may be too large to pass through the particle separating device 102, and so the additional UV photometry measurement when compared to the first UV photometry measurement may enable rapid determination of loss (or retention in the measurement platform 100) of proteins due to the particle separating device 102.

After the additional measurement is performed, the sample is flowed to a platform outlet 108, where it may be collected or disposed of.

Figure 3:
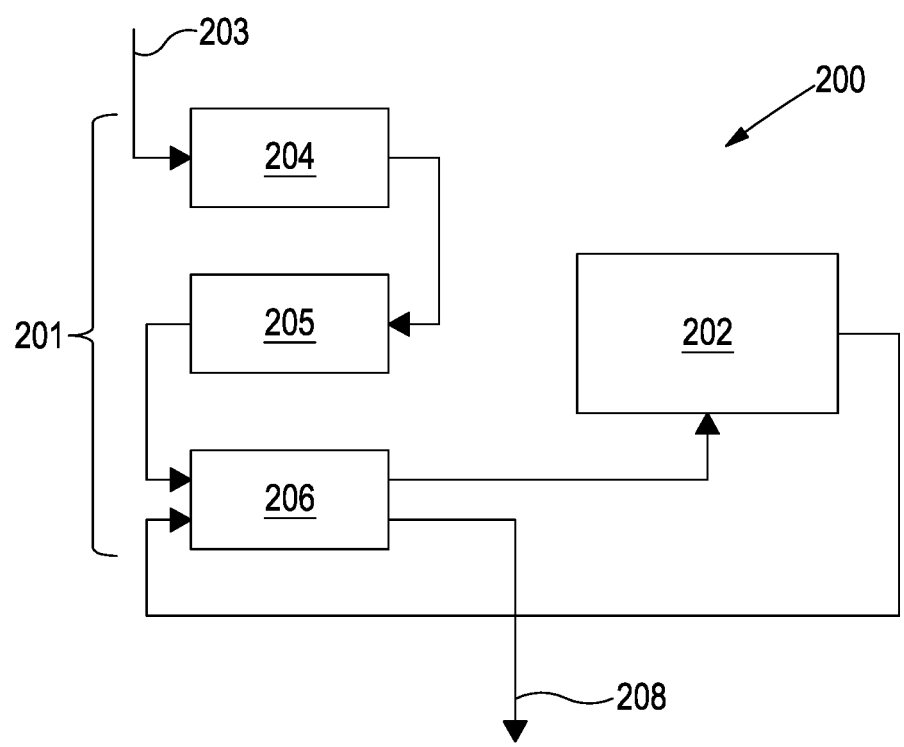
FIG. 3 is a schematic representation of an alternative particle characterisation platform.

In the platform 100 illustrated in FIG. 2, additional measurement system 107 is a separate measurement system to the first measurement systems 101. However, in alternative embodiments, the additional measurement may be performed by one of the first measurement systems 101. FIG. 3 shows such an example of such a platform 200.

Platform 200 comprises first measurement systems 201 and a particle separating device 202, similar to the corresponding features described above in relation to platform 100. Sample is flowed from the platform inlet 203 though each first measurement system 204-206 in series, each of which performs a first measurement, and then to the particle separating device 202. In contrast to platform 100, in platform 200 the sample is flowed from the particle separating device back to one (or more) of the plurality of first measurement systems 201. In this example the sample is flowed back to UV photometer 206, but it may be flowed back to any combination of the measurement systems. The UV photometer 206 performs an additional measurement on the separated sample, and the sample is then flowed to the platform exit 208. The first measurement performed by the UV photometer 206 may be directly compared to the additional measurement performed by the UV photometer 206 to determine if any particles or particle aggregates have been lost from the sample.

The flow of the sample through platforms 100, 200 may be controlled by valves. For example, at least one valve may be used to hold the sample in a particular system or device of the platform 100, 200 during measurements; and to release the sample when the respective measurement has been performed. The at least one valve may be manually or automatically operated.

Figure 4A:
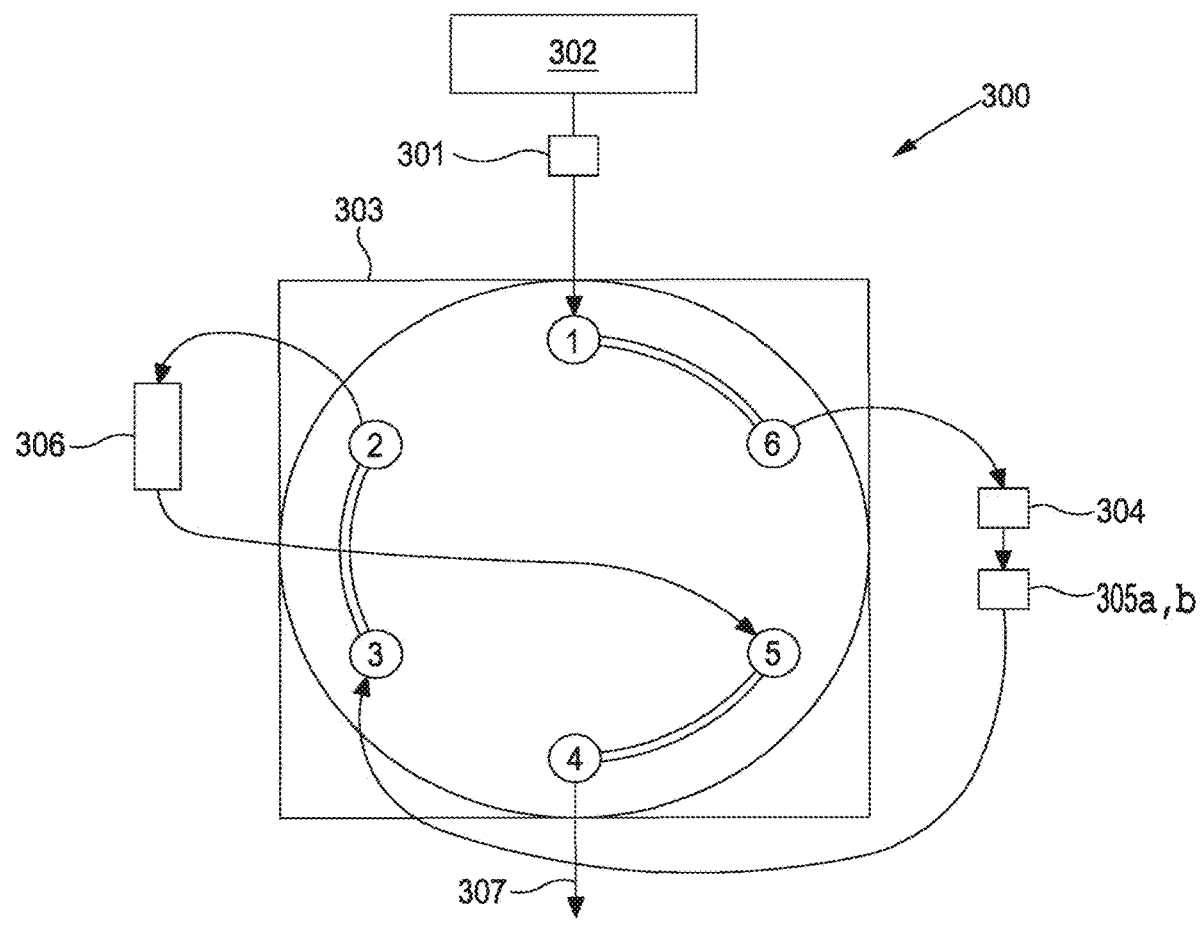
FIGS. 4a and 4b illustrate operation of a switch valve in a further alternative particle characterisation platform.
Figure 4B:
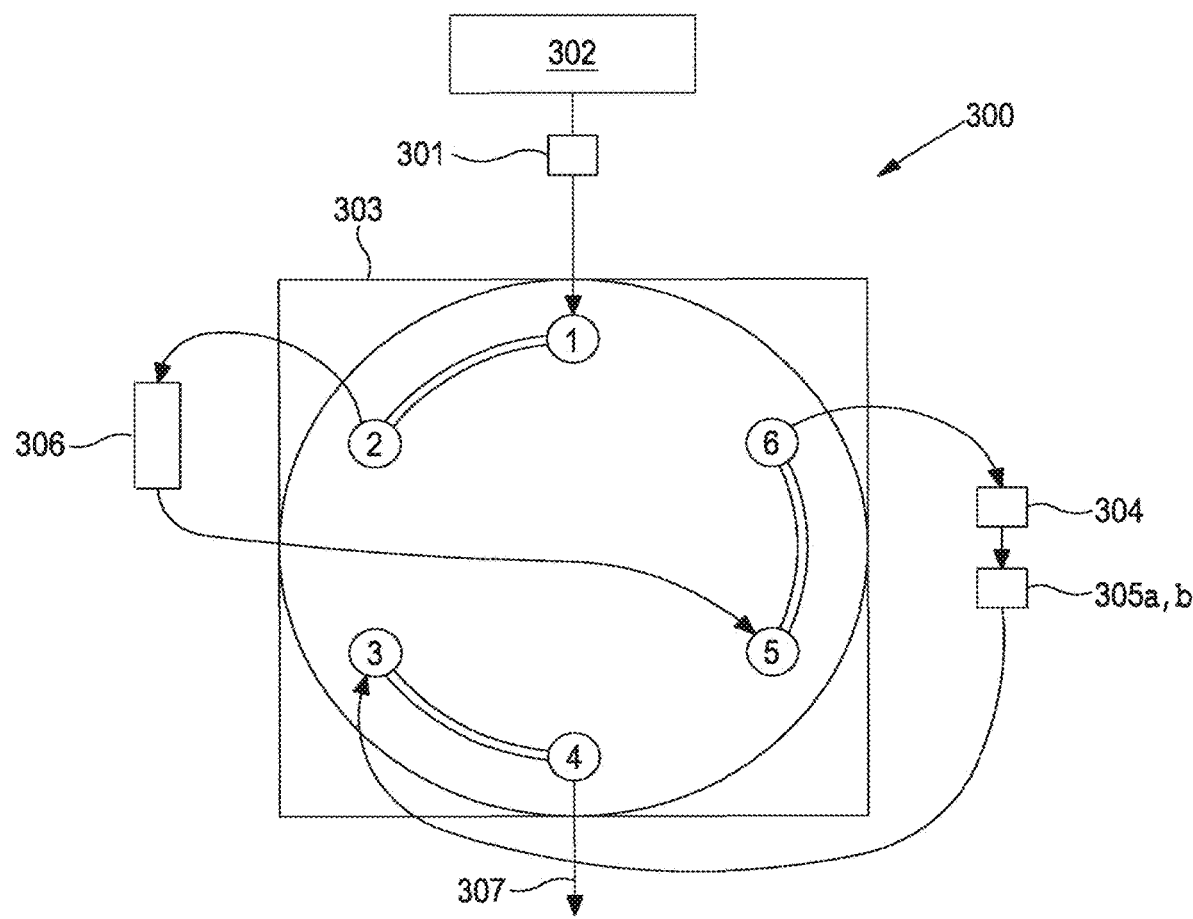

FIGS. 4a and 4b illustrate a platform 300 comprising a rheodyne switch valve 303, which controls the flow of sample through the platform 300. FIG. 4a shows the switch valve in a first configuration, and FIG. 4b shows the switch valve in a second configuration.

The switch valve is initially positioned in the first configuration. Sample is injected into the platform by injector 301, and pumped around the platform by pump 302. From the injector 301, the sample flows through tubing to connection 1 of the switch valve 303, which is connected to connection 6 in the first configuration. The sample flows from connection 6 to first measurement systems 304, 305. In the illustrated example, the first measurement instruments 304, 305 may comprise a UV photometer 304 and a light scattering system 305a, or a UV photometer 304 and a Taylor dispersion analysis system 305b (including a capillary loop). The light scattering system 305a may perform dynamic or static light scattering measurements on the sample as it passes though the light scattering system 305a. The first measurement systems 304, 305 perform first measurements on the sample, similar to those described above in relation to platform 100.

The sample then flows to connection 3 of the switch valve 303, which is connected to connection 2 in the first configuration, and then into particle separating device 306. Particle separating device 306, which may be a SEC instrument, separates and measures the sample as described above in relation to platform 100.

Before the sample elutes from the particle separating device 306, the switch valve 303 is moved into its second configuration, represented in FIG. 4b. Sample flows from the particle separating device 306 to connection 5 of the switch valve 303, which is now connected to connection 6 in the second configuration. This connection directs the sample back into the first measurement systems 304, 305, which perform additional measurements on the sample. These additional measurements may be used to determine if larger particles have been lost from the sample, as described above. From the first measurement systems 304, 304, the sample is flowed to connection 3 of the switch valve 303, and from there to a platform outlet 307 via connection 4 of the switch valve 303.

In the examples described above, the first measurement systems comprised two or three distinct systems. In alternative embodiments, any number of first measurement systems may be used, in particular only one first measurement system may be used. Thus in embodiments where the additional measurement is performed on the first measurement system, a platform may comprise only a first measurement system and a particle separating device, along with the tubing and valves necessary to direct the flow of the sample. Similarly, any number of additional measurements may be performed by any number of additional measurement systems, which may or may not be the same as the first measurement systems of the platform.

Figure 5:
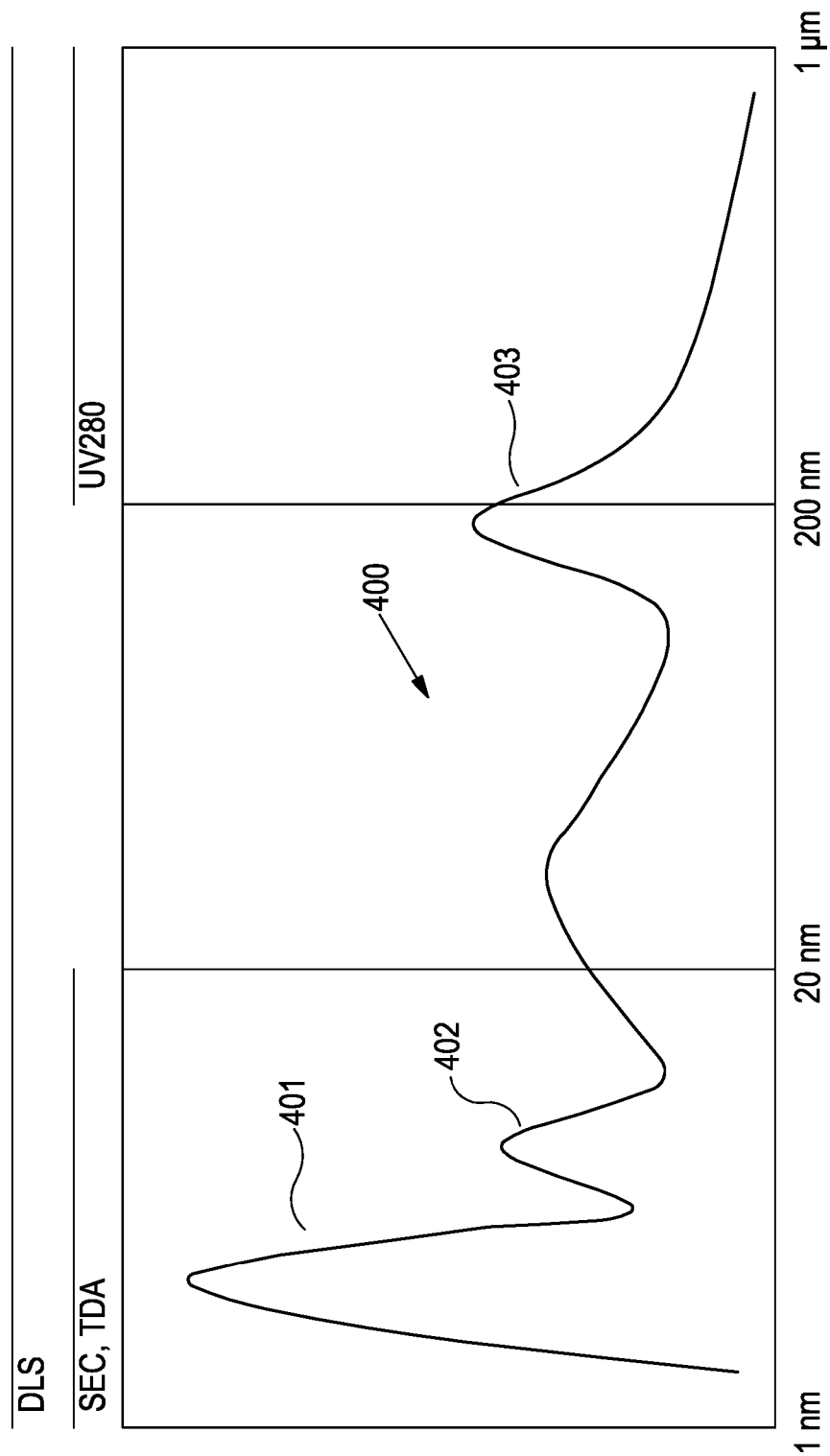
FIG. 5 illustrates a particle size distribution of a typical sample.

Advantageously, however, using a plurality of first measurement systems such as in platforms 100, 200 may provide a broader overall particle characteristic measurement window. FIG. 5 shows the particle size distribution 400 of a typical sample, extending over three orders of magnitude of particle size. The bars above the distribution 400 represent the particle size windows over which the particle characterisation techniques described above can measure. DLS is sensitive to particles over a large range of particle sizes, whereas SEC and TDA are limited to smaller particle sizes, and UV photometry at 280 nm is limited to larger particle sizes. The combination of particle characterisation techniques described above for platforms 100, 200 may thus provide complementary data on particle size, allowing a determination of the full particle size distribution.

The distribution 400 comprises distinct peaks 401, 402 and 403, representing monomers, dimers and larger aggregates respectively in the sample. Some of the aggregates in the aggregate peak 403 are larger than 200 nm in diameter. This is larger than a typical frit limit, which limits the largest size of particle that can enter an SEC column (a porous frit typically being used to limit the maximum particle size entering the SEC column, defining the frit limit). Thus the largest aggregates in this sample may not be able to pass through the particle separating device 102, 202, 302. In conventional systems, which use only a SEC measurement, these larger aggregates may not be identified. Using the platforms 100, 200, 300 described above, however, allows the larger aggregates to be identified by the first measurements, and so any loss of particles due to the particle separating device can be detected.

The particle characterisation technique used for the first measurement and the additional measurement may be, or comprise, a TDA measurement.

Taylor dispersion is a process by which shear flow is used to enhance the effective diffusivity of a sample. Laminar flow in a capillary results in a variation in flow velocity with radial location. Near the walls of the capillary the flow is substantially stationary, and at the centre of the capillary the flow velocity is at a maximum. This results in shearing of the adjacent lamina, which acts to enhance dispersion of a sample as it travels along the capillary.

In a typical TDA measurement, one or more detectors (responsive to the species of the sample) placed at fixed window positions along the capillary are used to detect the concentration of the sample in each cross-section of sample flowing past the or each detector window (typically by an optical absorbance measurement). The output from the or each detector is a temporally resolved concentration distribution (a Taylorgram). For a sufficiently long duration of travel along the capillary to the measurement window, such that the sample is fully dispersed, the Taylorgram profile approximates to a Gaussian distribution whose width ($\sigma$) is proportional to the hydrodynamic radius ($R_h$) by $$R_h = \frac{4k_B T}{\pi \eta r^2} \frac{\sigma^2}{\tau}, \tag{1}$$

where $k_B$ is Boltzmann's constant, T is the temperature, $\eta$ is the viscosity of the buffer solution, r is the radius of the capillary, and $\sigma$ is the residence time of the sample in the capillary (approximately the centre of the Gaussian).

Figure 6:
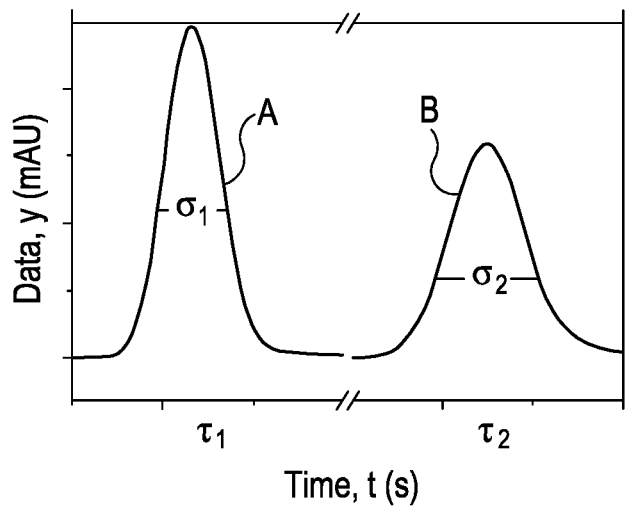
FIG. 6 illustrates a Taylor dispersion measurement.

FIG. 6 shows example Taylorgrams obtained at two separate measurement windows, A and B, along a capillary, where the residence time ($\tau_2$) of the second window B is greater than the residence time ($\tau^1$) of the first window A. As seen in FIG. 6, the width ($\sigma_2$) of the Taylorgram obtained at window B is greater than the width ($\sigma_1$) of the Taylorgram obtained at the window A, due to further dispersion along the capillary with time. In this case, $R_h$ is related to the widths $\sigma_1$, $\sigma_2$ and the residence times $t_1$, $t_2$ of the two Gaussians by $$R_h = \frac{4k_B T}{\pi \eta r^2} \frac{(\sigma_2^2 - \sigma_1^2)}{(\tau_2 - \tau_1)}. \tag{2}$$

The above two-window analysis is known to account for deficiencies in the single window analysis originating from a non-ideal initial sample profile (at t=0).

Where there are more than one species or population in the sample, the Taylorgram obtained at a given detector window comprises a superposition of concentration distributions for each species present.

In traditional TDA, e.g. pre-separation, the constituent components for each species each have the same residence time. An average $R_h$ for the obtained Taylorgram may be determined by fitting a single Gaussian. However, this may be imprecise due to the variety of possible solutions, especially where the width and amplitude of each constituent distribution differ to the extent that the Taylorgram no longer approximates well to a Gaussian. A more robust method of determining an average Rh for the Taylorgram is to analyse the moments of the distribution, which essentially involves the determination of the widths and centres of the Taylorgrams by computing the second and first moments of the distributions (via integration).

The zeroth moment of the Taylorgram, d(t), is the area integration, Area=∫d(t).dt, and yields the total concentration. The first moment divided by the Area yields the mean residence time, $$\bar{\tau} = \frac{\int t d(t) \cdot dt}{\int d(t) \cdot dt}. \quad (3)$$

The second moment divided by the Area yields the mean variance, $$\bar{\sigma}^2 = \frac{\int (t-\bar{\tau})^2 d(t) \cdot dt}{\int d(t) \cdot dt}. \quad (4)$$

Extracting the distribution corresponding to each separate species typically involves decomposing the obtained Taylorgram as sums of the constituent components corresponding to each species, e.g. by fitting multiple Gaussians, to extract σ for each component species comprising the Taylorgram (and hence $R_h$ for each species). However, in traditional TDA, e.g. pre-separation, multi-component analysis can also be imprecise due to the variety of possible solutions when the constituent components for each species each share the same residence time. For example, it is often difficult to distinguish monomer and dimer peaks, where the $R_h$ values may differ by as little as a few nm. This problem may be reduced by performing TDA after the sample has passed through the particle separating device 102, 202, i.e. post separation.

For a particle separating device that fractionates particles by size, after the sample has passed through the particle separation device 102, 202 the residence time for each differently sized sample component will not be the same, due to the variation of elution time with $R_h$. In this case, the constituent peaks for each species/component may be fully or at least partially resolved. Hence, performing TDA after the particle separation device can vastly improve the ability to extract a reliable Rh value for each species.

Figure 7:
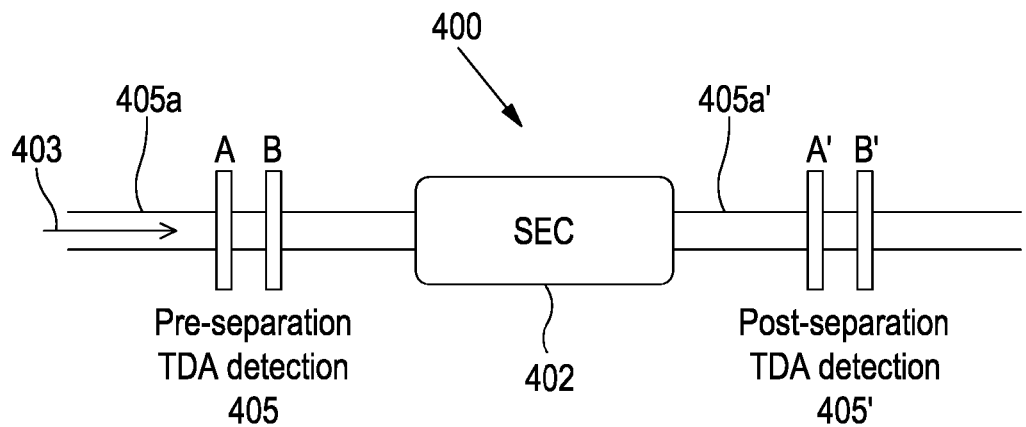
FIG. 7 is a schematic representation of a particle characterisation platform for combining SEC with Taylor dispersion analysis.

FIG. 7 shows a schematic representation of a particle characterisation platform 400 according to an embodiment of the invention. Platform 400 comprises a particle separating device 402, a first TDA measurement system 405 located upstream of the particle separation device 402 and a second TDA measurement system 405' located downstream of the particle separation device 402. A further measurement system such as a spectrophotometer or a photometer (e.g. a UV spectrophotometer or photometer) may be provided, for example for measuring species concentration immediately after exiting the particle separating device 402 (e.g. to perform a conventional SEC measurement).

The first TDA measurement system 405 comprises a capillary 405a, a first detector window A and a second detector window B, and the second TDA measurement system 405' comprises a capillary 405a', a first detector window A' and a second detector window B'. In use, a sample is flowed from an input 403 to the first TDA measurement system 405 where a first, pre-separation, TDA measurement is performed. The sample is then flowed to the particle separation device 402 to separate the sample based on a particle characteristic, such as particle size. After passing through the particle separation device 402, the sample is flowed to the second TDA measurement system 405' to perform a second, post separation, TDA measurement.

Although shown in FIG. 7 as separate measurement systems, the first and second TDA measurement systems 405, 405' may share the same detectors. For example, capillary 405a may be fed back through the detector windows A and B of the first TDA measurement system 405. It will be appreciated that other measurement systems may be included upstream and downstream of the particle separation device 402, as shown in FIGS. 2 and 3.

In the following, pre and post separation Taylorgrams are simulated for various sample mixtures to validate the proposed approach. In the simulations, the particle separation device 402 is assumed to be an SEC column and the Taylorgrams for each species are assumed to take on a Gaussian distribution. In this example, the detection windows A and B, and A' and B' are each separated by a difference in respective retention time of 720 seconds. The relative SEC column retention times (or elution times) t are assumed to correlate with $R_h{}^a$ (and hence molecular weight) by $t=a+bR_h{}^3$, where a is arbitrarily set to 2703 and b to −2.1 (an empirical match to a real measurement setup may be determined by experiment, using this function or some other representative function). The simulated Taylorgrams represent a light absorbance measurement performed at each detector window A, B, A', B'.

Figure 8A:
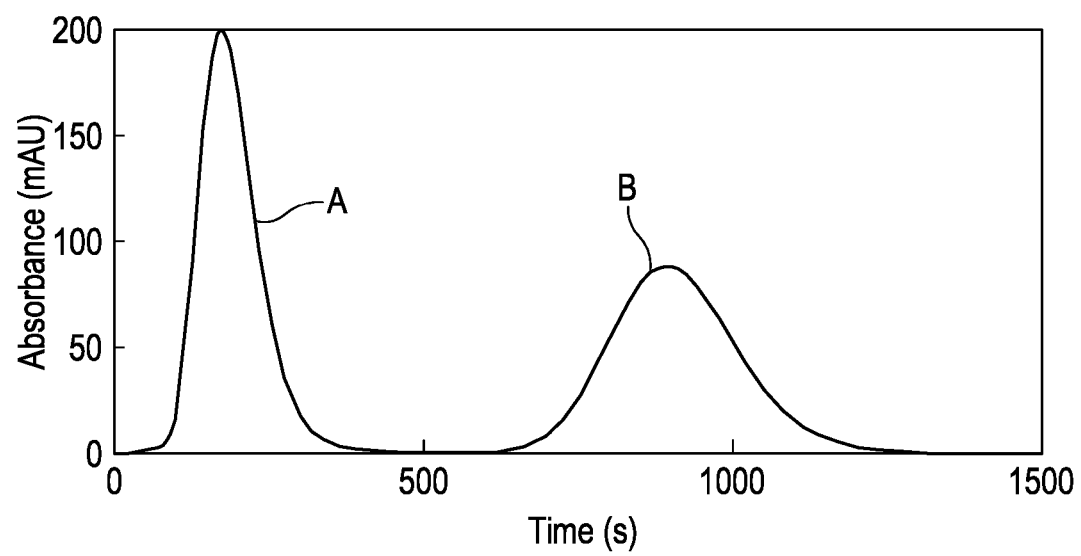
FIGS. 8a and 8b show, respectively, simulated Taylor dispersion measurements obtained before and after particle separation for a first test sample.
Figure 8B:
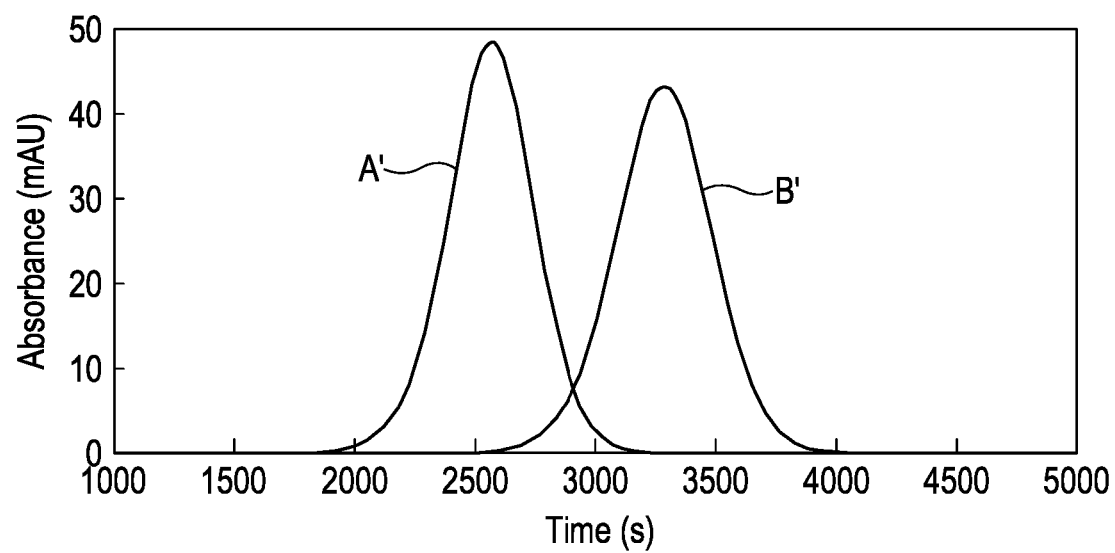

FIG. 8a shows pre-SEC Taylorgrams obtained at windows A and B of the first TDA measurement system 405 for a test sample 1 comprising monomeric bovine serum albumin (BSA) having an average particle size of 3.8±0.2 nm. FIG. 8b shows the corresponding post-SEC Taylorgrams obtained at windows A' and B' of the second TDA measurement system 405'. As there is only one species in the sample, the pre and post SEC Taylorgrams both exhibit a single distribution.

Figure 9A:
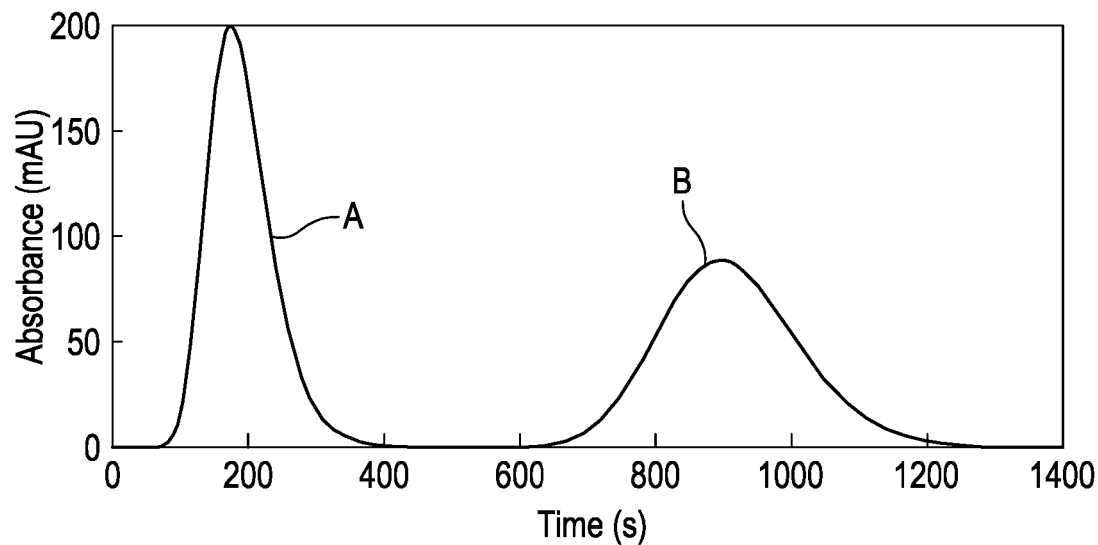
FIGS. 9a and 9b show, respectively, simulated Taylor dispersion measurements obtained before and after particle separation for a second test sample.
Figure 9B:
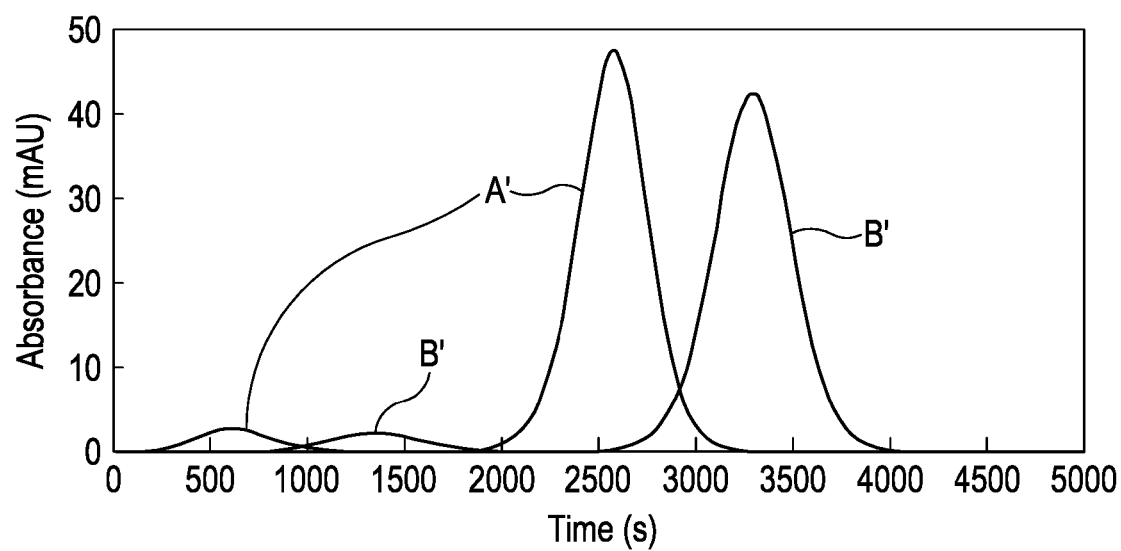

FIGS. 9a and 9b show, respectively, the pre and post SEC Taylorgrams for a test sample 2 comprising a mixture of BSA (3.8±0.2 nm) and eluted aggregates of 5.4 nm and 10 nm in size, in relative proportions of 80:15:5. Pre-separation, only a single peak is resolved in each detection window (see FIG. 8a). As shown in FIG. 9b, in the post-separation Taylorgrams A' and B', additional peaks at shorter retention times are resolved, corresponding to one or more of the additional aggregates.

Figure 10A:
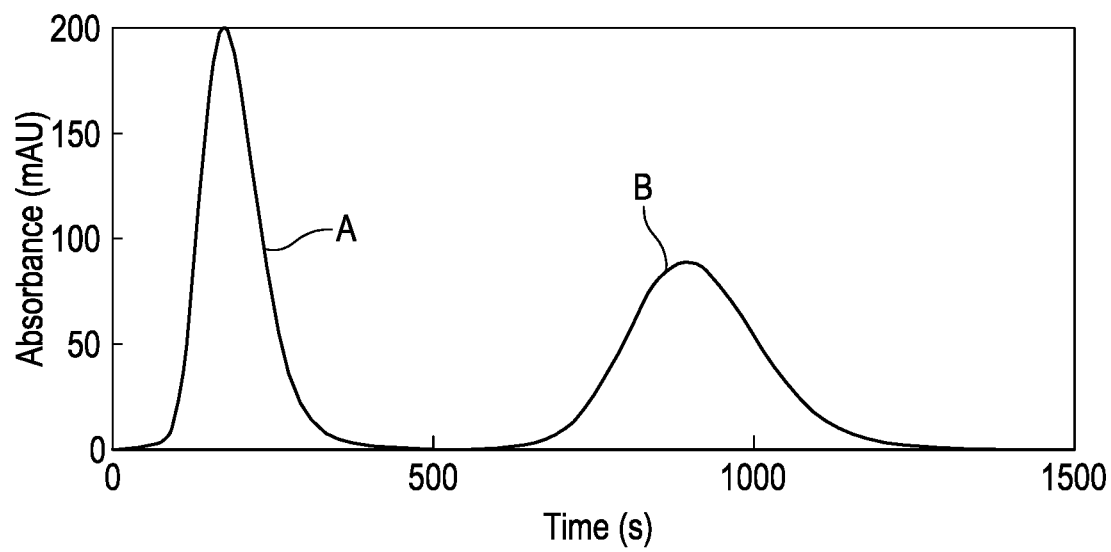
FIGS. 10a and 10b show, respectively, simulated Taylor dispersion measurements obtained before and after particle separation for a third test sample.
Figure 10B:
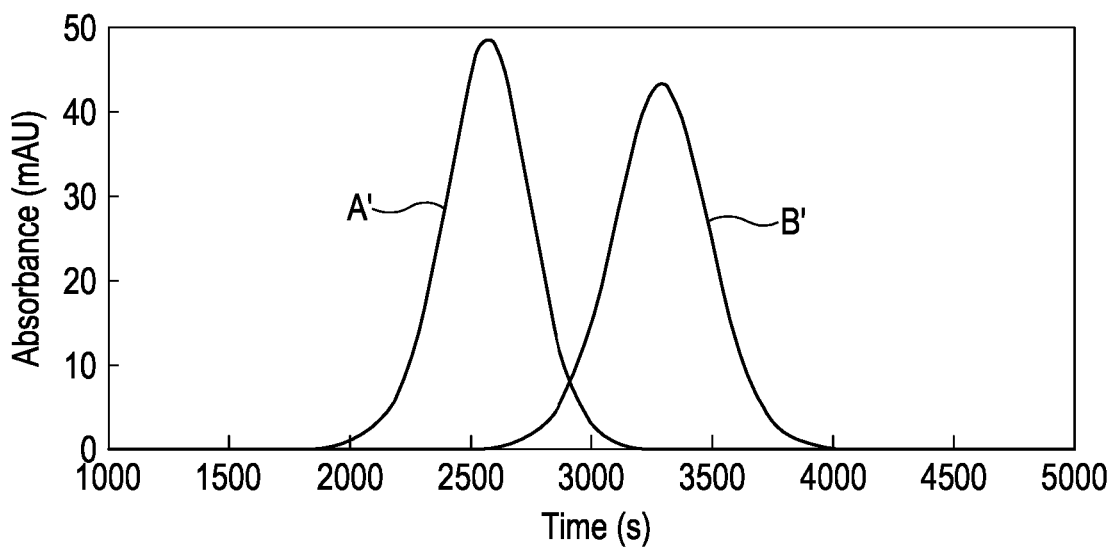

FIGS. 10a and 10b show the results of the simulation for a test sample 3 comprising a mixture of BSA (3.8±0.2 nm) and eluted aggregates of 5.4 nm and 60 nm in size, in the same relative proportions of 80:15:5. In this case, the SEC column excludes the 60 nm particles and no short retention time peak is observed. Separate distributions for BSA and the 5.4 nm aggregate are superposed and not resolved in the post-SEC Taylorgrams A' and B'.

TABLE 1

| Sample mixture | $R_h$ (nm) Pre-SEC | $R_h$ (nm) Post-SEC | Area (mAUs) Pre-SEC | Area (mAUs) Post-SEC | Remarks |
|---|---|---|---|---|---|
| 1) 3.8 ± 0.2 nm | 3.81 | 3.81 | 21561 | 21561 | 100% purity |
| 2) 3.8, 5.4, 10 nm (85%, 15%, 5%) | 4.36 | 4.37 | 22527 | 22526 | Eluted aggregate |
| 3) 3.8, 5.4, 60 nm (85%, 15%, 5%) | 6.44 | 4.06 | 22861 | 21817 | Excluded 60 nm component |

The relative change in the computed moments (equations 3 and 4) post-SEC gives an average $R_h$ which can be compared to the average $R_h$ value pre-SEC. (Note that post-SEC, the moment method cannot work on a single window because the standard deviation/second moment would be wrong and overestimated due to the separation. However, the difference between the values at two windows is independent of the separation).

Table 1 above shows the weighted average value of $R_h$ and the area under the Taylorgram (which is proportional to the concentration of particles) obtained from pre and post particle separation simulations of each test sample using moment analysis with equations 2-4. As shown, the pre and post-SEC weighted average values of $R_h$ for test samples 1 and 2 match well. This provides an indication that no particles have been lost during separation. A comparison of the pre and post-SEC areas provides an additional or alternative indicator confirming this. By contrast, the pre and post-SEC weighted average values of $R_h$ and areas for test sample 3, which comprised the larger 60 nm particles, do not match. This provides an indication that particles have been lost during separation.

Additionally or alternatively to determining average $R_h$ values (e.g. using moments), or $R_h$ values for each constituent component by fitting multiple Gaussians, non-negative least squares (NNLS) analysis of a Taylorgram may be used to extract particle size distributions for the or each species present in the sample. Advantageously, NNLS analysis of post particle separation Taylorgrams may also yield more resolved particle distributions, as demonstrated below.

The NNLS method is a fitting method that aims to find a non-negative solution set to the following equation:

$$F*A=d, \quad (5)$$

where A is an array of the coefficients (or proportions) of arbitrary functions f which make up a matrix F. The result of the matrix multiplication is the composite distribution d. Hence if F is an m×n matrix (i.e. there are n functions of a variable of length m), A is an n×1 array and d is an m×1 array. Typically, an exact solution to equations 5 cannot be found, so instead an optimal solution is obtained by minimizing the norm of the residuals, $\|F*A-d\|^2$, with the condition that the elements of A are greater than or equal to zero (i.e. non-negative).

In this case, d is the time-dependent Taylorgram. For pulse Taylorgrams where the sample is fully dispersed, the function F comprises time-dependent Gaussians of the form:

$$F = \sqrt{\frac{t_0}{t}} e^{-\left[\frac{(t-\tau)^2}{2\sigma^2}\frac{t_0}{t}\right]}, \quad (6)$$

where t is the time of the measurement, $\tau$ is the residence time and $\sigma$ is the width from which the $R_h$ of the sample is determined (e.g. from equation 1 or 2). A is an array of the coefficients of each time-dependent Gaussian which gives the contribution of the function F to the Taylorgram, d. As such, A is known as the particle size distribution. Below is an example for a two-component Taylorgam:

$$\begin{bmatrix} f(\sigma_1, \tau_1, t_1) & f(\sigma_2, \tau_2, t_1) \\ f(\sigma_1, \tau_1, t_2) & f(\sigma_2, \tau_2, t_2) \\ \vdots & \vdots \end{bmatrix} \begin{bmatrix} A_1 \\ A_2 \end{bmatrix} = \begin{bmatrix} d(t_1) \\ d(t_2) \\ \vdots \end{bmatrix} \quad (7)$$

Each column of F is the time-dependent Gaussian for each component of the Taylorgram (i.e. each species present in the sample). Equation 5 (or 7) may be solved for A by multiplying both sides from the left by the inverse of F, $$A = F^{-1}*d. \quad (8)$$

In conventional pre-separation NNLS analysis of TDA measurements, it is assumed that all the functions F have the same residence time, e.g. $\sigma_1$, $\tau_2 = \tau$. For post-separation analysis, however, each function F is assumed to have a different residence time, e.g. $\tau_1 \neq \tau_2$.

In the NNLS fitting process, $R_h$ is scanned across a range of values to determine the best fit of equation of 5 or 7 to the experimental data. The number and range of $R_h$ values scanned for at a particular residence time may be user defined, but can be estimated a priori. In an idealised experimental set-up, such as that shown in FIG. 7, there is a known a priori correlation between the Taylorgram widths and the residence time that can be used to limit the range of $R_h$ scanned for at a particular residence time. For example, in SEC, there is a correlation between molecular weight and the residence time. The correlation may be known, or may be determined from an initial calibration step whereby a range of samples with known $R_h$ values are analysed to determine their residence times. In the following results, the correlation $t=a+bR_h^3$ is assumed (as used for the initial simulations).

Figure 11A:
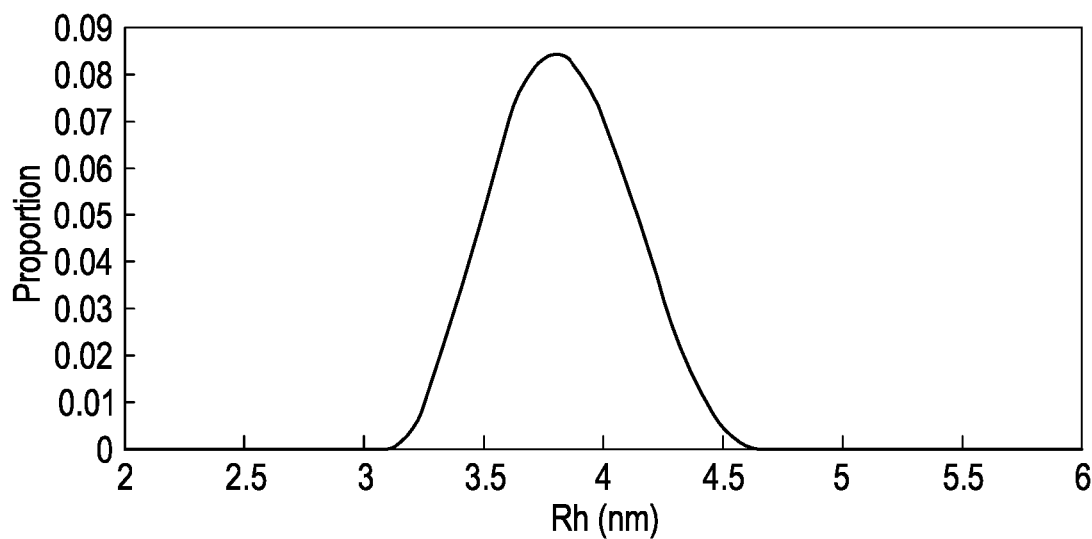
FIGS. 11a and 11b show particle size distributions obtained from the simulated data of FIGS. 8a and 8b, respectively.
Figure 11B:
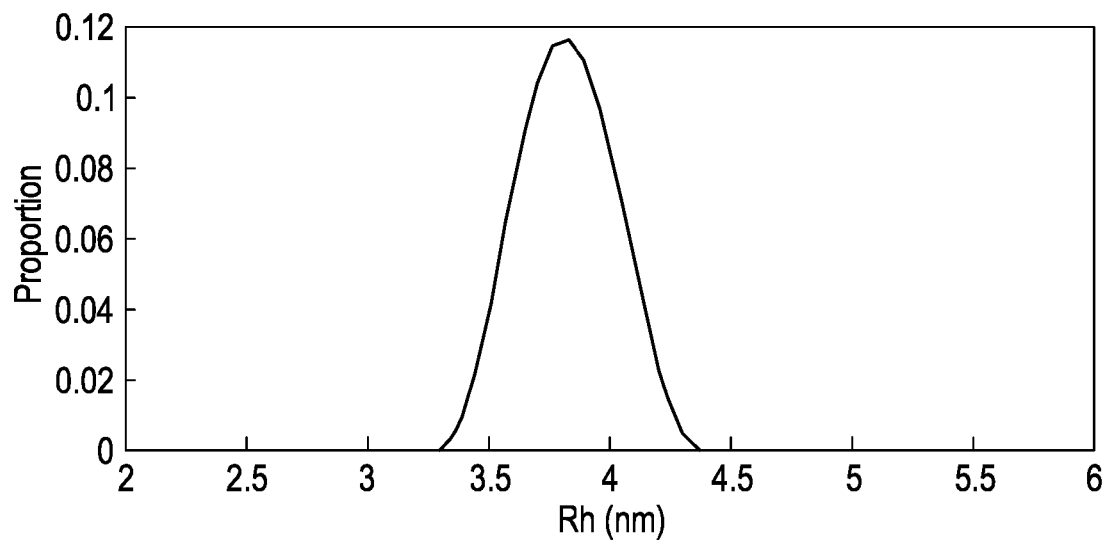
Figure 12A:
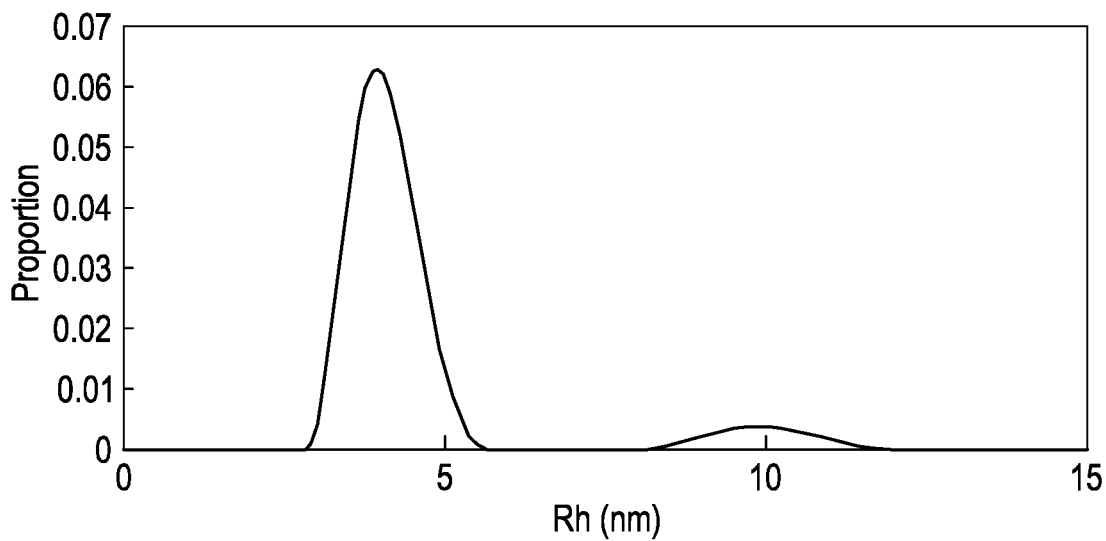
FIGS. 12a and 12b show particle size distributions obtained from the simulated data of FIGS. 9a and 9b, respectively.
Figure 12B:
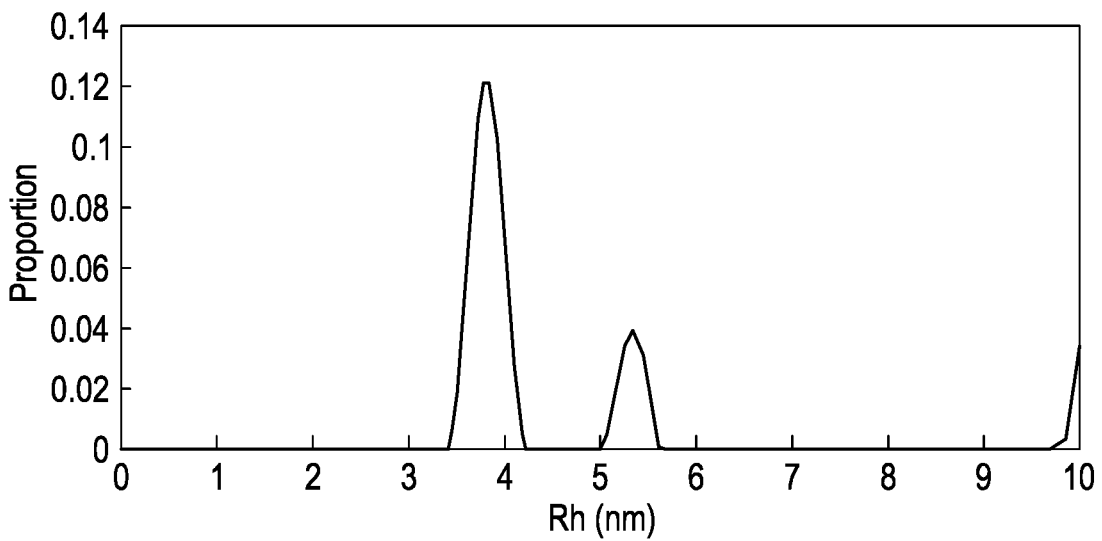

FIGS. 11a and 11b show the pre-SEC and post-SEC particle size distributions extracted from the Taylorgrams of FIGS. 8a and 8b (for test sample 1), respectively, using the NNLS method. The Taylorgrams at windows A' and B' yield the same result (not shown). Both pre-SEC and post-SEC particle distributions exhibit a peak at approximately 3.8 nm, in good agreement with the BSA size. FIGS. 12a and 12b show the corresponding pre-SEC and post-SEC particle size distributions extracted from the Taylorgrams of FIGS. 9a and 9b, respectively (for test sample 2). As seen in FIG. 12a, in the pre-SEC particle distribution, a peak at approximately 10 nm is resolved, but the distributions for the BSA (3.8 nm) and 5.4 nm particles cannot be distinguished from each other. By contrast, in the post-SEC particle distribution separate peaks for BSA (3.8 nm) and the 5.4 nm particles are clearly resolved.

Figure 13A:
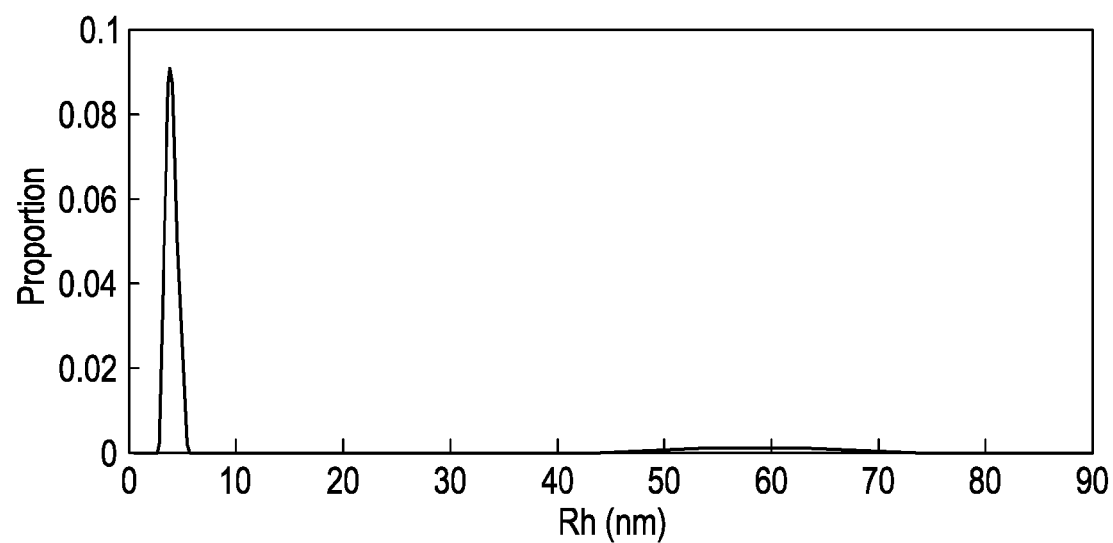
FIGS. 13a and 13b show particle size distributions obtained from the simulated data of FIGS. 10a and 10b, respectively.
Figure 13B:
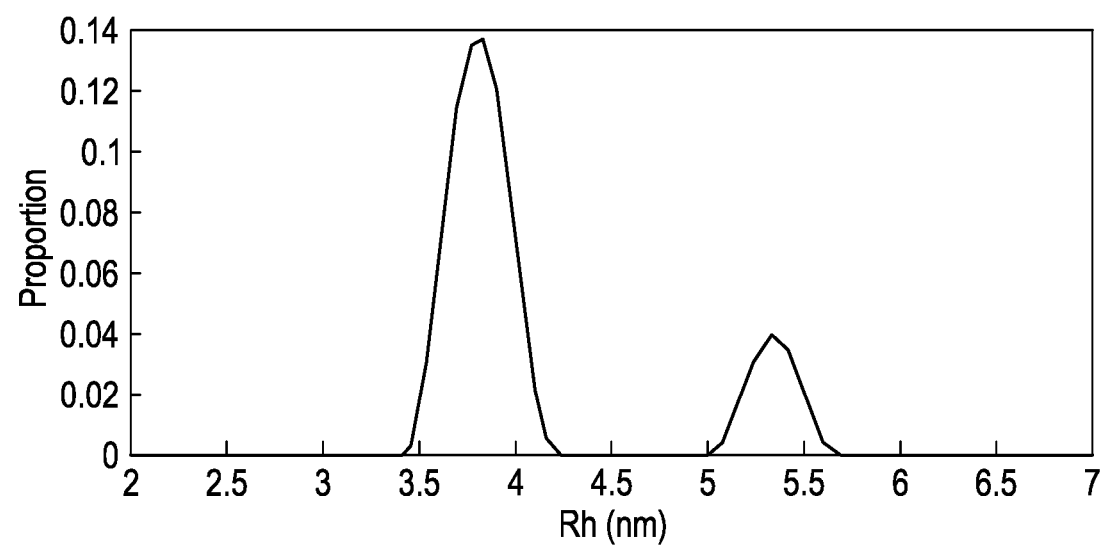

FIGS. 13a and 13b show the pre-SEC and post-SEC particle size distributions extracted from the Taylorgrams of FIGS. 10a and 10b (for test sample 3), respectively. The pre-SEC particle distribution (FIG. 13a) a peak at approximately 60 nm is resolved, but the BSA (3.8 nm) and 5.4 nm peaks cannot be distinguished from each other. In the post-SEC particle distribution, as with the results for test sample 2, the peaks for BSA (3.8 nm) and the 5.4 nm particles are clearly resolved, but in this case, no peak at 60 nm is observed due to the 60 nm particles being excluded in the SEC column.

The above NNLS method relies on a priori knowledge of the correlation between the post-separation residence time and the $R_h$ of the components. This may be calibrated by a reference measurement, as discussed above. In addition, the expected Taylorgram width at a particular residence time may not be the same as expected for traditional pre-separation TDA because of the geometry of the column. This effect may also need to be determined from a reference measurement. By contrast, analysing multi-component post-separation Taylorgrams by fitting multiple Gaussians is relatively straightforward and requires no a priori knowledge of the correlation between Taylorgram widths and the residence time.

Alternatively or additionally, the residence time may be adjusted to match the dispersion observed between two consecutive measurement window (e.g. windows A' and B').

The above examples demonstrate the merits of the proposed method. Pre and post separation TDA provide orthogonal results that may be used to verify or augment the results of an SEC measurement. Although the above examples analyse and compare pre and post-SEC TDA measurements, it will be appreciated that this is just one example of comparing a first measurement performed before particle separation with a second measurement performed after particle separation. Similar results may be obtained with other measurements techniques, such as UV photometry and DLS, for example. In particular, the above NNLS fitting method may also be applied to DLS measurements performed before and after particle separation.

In some embodiments, the first particle characterisation technique may comprise UV spectrometry and static light scattering, the particle separating device may comprise a chromatography column (e.g. an SEC column), and the second particle characterisation technique may comprise UV spectrometry and static light scattering.

For example, an Omnisec Resolve or similar instrument may be used to provide the first characterisation technique and the second characterisation technique. The sensing modalities in the Omnisec Resolve comprise four detector types, which are listed below. In principle, either or both of the refractive index detector and viscometer may be omitted.

Detector 1

Detector: Light scattering
Measurement principle: Right angle light scattering (RALS) at 90° scattering angle, Low angle light scattering (LALS) at 7° scatter angle
Light source: 640 nm laser

Detector 2

Detector: Differential refractive index
Measurement principle: Deflection
Cell volume: 12 µL

Detector 3

Detector: Viscometer
Measurement principle: 4-capillary Wheatstone bridge with self-balancing mechanism and user-exchangeable capillaries

Detector 4

Detector: Diode-array-based UV/Vis spectrometer
Wavelength: 190-900 nm
Number of wavelengths: 1024
Wavelength accuracy: <1 nm
Wavelength resolution: 0.6 nm The four different detector types may be used to perform a number of different measurement types.

Measurement Type 1

Measurement type: Absolute molecular weight
Measurement range: 200→107 g/mol
Minimum quantifiable mass: 100 ng of 100 kDa molecular weight polystyrene in THF
Measurement principle: Light scattering (LALS or RALS)

Measurement Type 2

Measurement type: Intrinsic viscosity
Minimum quantifiable mass: 1 µg of 100 kDa molecular weight polystyrene in THF
Measurement principle: 4-capillary Wheatstone bridge

Measurement Type 3

Measurement type: Concentration
Minimum quantifiable mass: 100 ng of 100 kDa molecular weight polystyrene in THF
Measurement principle: Differential refractive index detection The particle separation device may comprise an Omnisec Reveal with a chromatography column. This provides an automated HPLC system for particle separation using chromatography. In other embodiments, any chromatography system may be used for particle separation (e.g. liquid chromatography systems with pressures greater than 40 MPa).

A hybrid workflow comprising separate SEC analysis, light scattering analysis and optical microscopy analysis may be compared with an automated system in which a light scattering and UV-Vis spectrographic measurement (e.g. a light absorption measurement) is made on the same sample, before and after it flows through an SEC column.

The time taken to perform a measurement and synthesise a result for an embodiment may be around 5 times faster than a typical hybrid workflow.

Quantitative ratios of particles in each of a number of categories may be determined. The categories may comprise:
 LMW/fragments (particles with size or molecular weight smaller than the monomer),
 monomer,
 HMW/aggregates (with size or molecular weight larger than the monomer, such as dimers, trimers and other oligomers), and
 VHMW (very high molecular weight particles or particles with very large size).

The quantitative ratios may comprise a particle mass based concentration (e.g. based on absorption ratios).

The VHMW quantity may be inferred from a difference in total absorption before and after separation (e.g. from the area under an absorption peak before separation, minus the total area under absorption peaks after elution through the separation device/SEC column).

The ratios of LMW, monomer and HMW may be inferred from a combination of light scattering (which provides information on the particle size or molecular weight for each component of the separated sample as it passes the light scattering detector) and the UV photometric measurements, which provides a quantitative measure of concentration of each component. For example, a combination of elution time and light scattering measurements may be used to classify each peak in an eluted UV photometric measurement as belonging to LMW, monomer or HMW. The difference in total concentration before and after separation may be used to provide the VHMW concentration.

At its simplest, a UV photometric measurement may be used to infer the various ratios in each of the above mentioned categories. If the elution time of the monomer is known, peaks eluted earlier than this can be classified as LMW, and peaks after this as HMW (with the peak at the expected elution time being the monomer). Any "missing" concentration (absorption present before separation but not after) may be attributed to VHMW.

Some information may be possible to infer about the VHMW without any further measurement modality (other than UV photometry before and after separation). For example, the size of the VHMW particles must be large enough not to be admitted to, or to not pass through the separation device. This may allow a minimum particle size to be inferred (e.g. based on a frit size at a column input).

However, it may be preferable to be able to obtain more information about the characteristics of the VHMW component of the sample, such as the average particle size (e.g. Dv50), polydispersity or particle size distribution of this component. A light scattering measurement (e.g. static light scattering or dynamic light scattering), performed before and after separation, is one way this can be achieved. The characteristics of the scattered light before separation can be compared with the characteristics of scattered light after separation. Information about the LMW, monomer and HMW components may be inferred from the second measurement (after separation). Once the scattering contribution from the LMW, monomer and HMW components are known, the scattering contribution from the VHMW component can be inferred, and this scattering contribution used to characterise the VHMW component (e.g. to provide an average particle size, polydispersity, or particle size distribution for the VHMW component).

Experiments performed based on these principles have been performed, and compared with prior art hybrid measurement approaches, and found to give good agreement.

Figure 14:
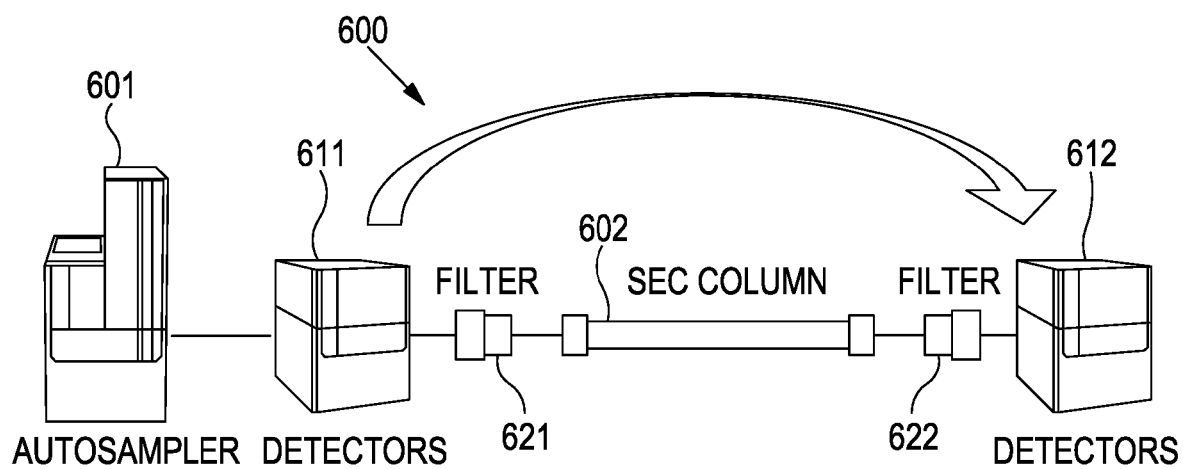
FIG. 14 is a schematic of a platform according to an embodiment.

FIG. 14 illustrates an example embodiment of a particle characterisation platform according to an embodiment, comprising: autosampler 601, first measurement system 611, first filter 621, SEC column 602, second filter 622 and second measurement system 612.

The autosampler 601 is configured to receive a plurality of samples, such as HPLC vials or a microtitre plate, and to automatically inject samples onto a column via the first measurement system 611 to be eluted by an eluent liquid so as to perform liquid chromatography.

The first measurement system 611 and the second measurement system 612 comprise a UV photometer and a scattered light detector (e.g. right angle scatter or low angle scatter). The platform 600 is configured to flow the sample through the first measurement system 611, through the SEC column 602, then through the second measurement system 612. In some embodiments the output from the SEC column 602 may be redirected back to the first measurement system 611 for the second measurement (and the second measurement system 612 omitted).

Figure 15:
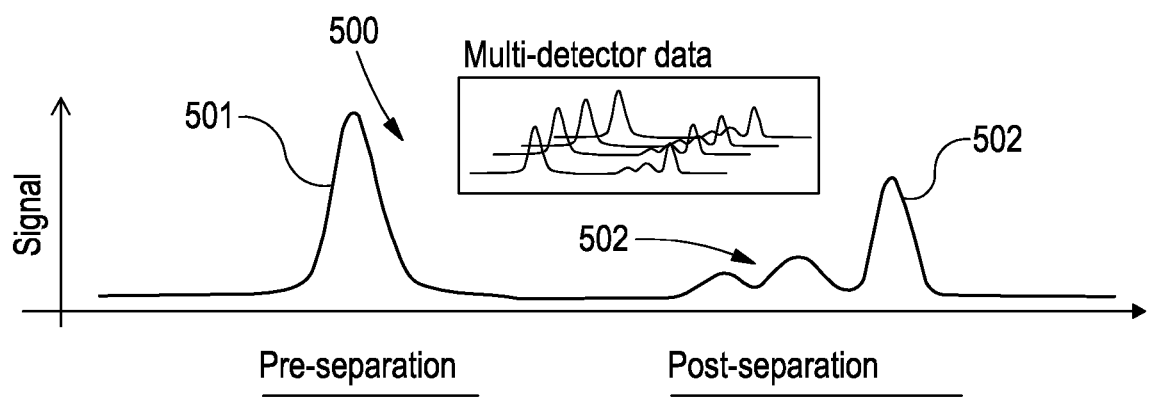
FIG. 15 is an example of a combined measurement produced from the first and second measurement.

A schematic example of a chromatogram 500 obtained in accordance with an embodiment is illustrated in FIG. 15. In this example the chromatogram signal may be assumed to be UV absorption, and comprises a pre-separation peak 501 comprising all the sample components (including any large particles not compatible with the separation process). The chromatogram 500 further comprises signal peaks 502 post-separation. Each of these post-separation peaks corresponds with a component of the sample. For the example where the first measurement comprises both a UV photometric measurement and a scattering measurement, the measurement data may comprise two chromatograms: one for UV absorption (i.e. a UV chromatogram), and one of scattering intensity (which may be termed a scattering chromatogram).

An example workflow for quantitative analysis of the proportion of particles in the same in different categories will now be described.

The UV chromatogram may first be subsampled, in order to reduce computational overhead. This is not essential, but speeds things up. Subsampling may be helpful in reducing the time taken to fit a baseline to the data and to identify peaks. The full dataset may be used to determine peak areas, in order to maintain accuracy.

A baseline may be fitted to the data, and significant peaks identified (e.g. by finding local maxima in the data). An active region of the chromatogram may be defined with reference to the location of the maximum peak, which in an aggregation study should correspond with the monomer of interest. The active region may be defined with reference to the location and width of the maximum peak, so as to be responsive to the characteristics of the monomer under analysis. For example, the active region may start at the location of the maximum peak minus a predetermined number of maximum peak widths, and end at the location of the maximum peak plus a predetermined number of maximum peak widths.

The data in the active region may be passed to a deconvolution algorithm, which performs a full fit of time separated pseudo-Gaussian profiles to the data:

$$y = \sum_{i=1}^{i=n} A_n \sqrt{\frac{c_n}{t}} \, e^{\frac{c_n}{t}\left(\frac{t-c_n}{\sqrt{2}\,\sigma_n}\right)^2}$$

The unknowns are the amplitudes $A_n$ and widths $\sigma_n$ which can be solved for by fitting profiles at a range of centre times $c_n$ until a best-fit is found to the data. This can be achieved with a non-negative least squares fit which solves the following matrix equation:

$$y = T.A$$

$$\Rightarrow A = T^{-1}.y$$

where in this representation, T is a matrix of unit amplitude pseudo-Gaussians with selected combinations of widths and centre times, y is the chromatogram data and A is the vector of amplitudes to be solved for.

The centre times and widths to be scanned for may be pre-selected. To speed up the computation time, centre times spaced by half the width of the identified monomer peak may be used in the decomposition. The initial estimates for the width array may be log-spaced from $1/\sqrt{8}$*monomer width to 2*monomer width.

The regions of the chromatogram corresponding with the monomer, fragments and aggregates can be determined from the fitted solution. The first significant shoulder to either side of the monomer peak may be identified as the end of the monomer region.

Significant shoulders may be identified when:
i. the prominence of a turning point in the gradient is >0.5% of the maximum prominence; or
ii. the turning point is a broad peak with a prominence>0.1% of the maximum and has a half-width greater than a fifth of the estimated monomer width; or
iii. either of conditions (i) and (ii) are satisfied and the shoulder is greater than a distance of 1.2*monomer width from the monomer peak maximum. This is to ensure that spurious shoulders around the maximum are not picked up.

Once the peaks in each region have been identified and fitted, it is straightforward to determine the sum of the areas in each region, and convert this into percentages reflecting the concentration of each proportion in the sample.

It may be advantageous to use the UV chromatograph to identify the regions of the chromatograph (i.e. the elution times corresponding with these components of the sample), and to then apply these to the scattering chromatogram.

For each peak (corresponding with a sample component), the ratio of the area of the UV chromatograph and the scattering chromatograph may be calculated in order to provide an estimate of particle size/relative molecular weight for that peak.

The pre-separation measurement data can be treated as combination of a linear fit (to remove the baseline) a pseudo-Gaussian (e.g. a time dependent Gaussian) fitted to the pre-separation UV absorption peak.

The area under this peak may be compared with a total area under the post separation UV absorption peaks to provide information about any potential VHMW component present in the sample. A discrepancy between the total UV absorption before separation and after separation is not always attributable to VHMW content in the sample. In some cases there may be losses of aggregate, monomer or fragments in the separation device/SEC column, which will lead to a difference in total absorption before and after separation that is not attributable to VHMW particles.

In order to avoid false identification of VHMW particles, a secondary indicator for VHMW particles may be used. The secondary indicator may comprise a threshold for a discrepancy in total signal (e.g. in UV absorbance or scattering). A discrepancy in UV absorption of at least 5% or at least 10% may be indicative of VHMW particles. A discrepancy in total scattered light (i.e. a difference in the area under the scattered light intensity signal before and after separation) may also be indicative of VHMW particles. Since larger particles scatter light more strongly, light scattering may be more sensitive to large particles, and relatively large discrepancies (e.g. of greater than 40% or greater than 50%) may be observed in light scattering before and after separation when VHMW particles are present. Combining both UV absorption discrepancies with total scattering discrepancy provides a relatively reliable indication of VHMW particles. For example, if there is 5% or greater discrepancy in UV absorption and a 40% or 45% or greater discrepancy in total scattering, it may be inferred with a high degree of confidence that VHMW particles are responsible.

An alternative secondary indicator for establishing that VHMW particles are causing a discrepancy in total signal (e.g. absorbance or scattering) in pre and post separation measurements is to review the average molecular weight determined from the pre and post separation analyses. A discrepancy in average molecular weight in excess of a particular threshold may indicate VHMW particles. The threshold may be, for example 2 or 2.2.

If a secondary indicator is present, the difference in UV absorption before and after separation can be used to estimate the mass proportion of the sample that comprises VHMW particles. Discrepancies in UV absorption that are not accompanied by a secondary indicator of VHMW particles may be ignored (and the proportions of fragments, monomer and aggregates based only on the second measurement, post separation).

Other embodiments are intentionally within the scope of the invention as defined by the appended claims.

The invention claimed is:

1. A method of characterising a sample comprising particles, the method comprising:
performing a first measurement on the sample using a first particle characterisation technique;
flowing the sample from the first particle characterisation technique to a particle separator;
separating the sample with the particle separator;
performing a second measurement on the separated sample; and
comparing the first measurement and the second measurement to determine if all the particles of the sample have passed through the particle separator, wherein comparing the first measurement and second measurement comprises:
determining if the second measurement matches the first measurement; and
if the second measurement does match the first measurement, determining that all particles of the sample have passed through the particle separator; and
if the second measurement does not match the first measurement, determining that not all of the particles of the sample have passed through the particle separator.

2. The method of claim 1, wherein the particle separator comprises a chromatography column, and optionally wherein the chromatography column is a size exclusion chromatography column.

3. The method of claim 1, further comprising determining a particle characteristic distribution of the sample, and optionally wherein the particle characteristic is particle mass or particle size.

4. The method of claim 1, further comprising flowing the sample from the separator device back to the first particle characterisation technique.

5. The method of claim 1, wherein performing the second measurement comprises performing the second measurement on the sample using the first particle characterisation technique.

6. The method of claim 1, further comprising performing an additional measurement on the sample before separating the sample with the particle separator, after separating the sample with the particle separator, or before and after separating the sample with the particle separator.

7. The method of claim 6, wherein performing the additional measurement comprises: performing an additional measurement on the sample using the first particle characterisation technique; or performing an additional measurement on the sample using a second particle characterisation technique, the second particle characterisation technique being different from the first particle characterisation technique.

8. The method of claim 1, wherein flowing the sample from the first particle characterisation technique to the particle separator comprises operating a valve to direct the sample from the first particle characterisation technique to the particle separator.

9. The method of claim 1, wherein the first particle characterisation technique, the second particle characterisation technique, or both the first and second particle characterisation techniques comprises one or more ensemble particle characterisation technique.

10. The method of claim 9, wherein the one or more ensemble particle characterisation technique is selected from the group comprising: UV spectroscopy, dynamic light scattering, static light scattering, and Taylor dispersion analysis, and UV photometry.

11. A particle characterisation platform comprising:
a sample measurer configured to perform measurements according to a first particle characterisation technique; and
a particle separator configured to separate samples comprising particles;
wherein the particle characterisation platform is configured to:
perform a first measurement on the sample with the sample measurer using a first particle characterisation technique;
flow the sample from the sample measurer to the particle separator;
separate the sample with the particle separator;
perform a second measurement on the separated sample; and
compare the first measurement and the second measurement to determine if all the particles of the sample have passed through the particle separator, wherein comparing the first measurement and second measurement comprises:
determining if the second measurement matches the first measurement; and
if the second measurement does match the first measurement, determining that all particles of the sample have passed through the particle separator; and
if the second measurement does not match the first measurement, determining that not all of the particles of the sample have passed through the particle separator.

12. The particle characterisation platform of claim 11, wherein the particle separator comprises a chromatography column, and optionally wherein the chromatography column is a size exclusion chromatography column.

13. The particle characterisation platform of claim 11, wherein the sample measurer is further configured to perform measurements according to a second particle characterisation technique.

14. The particle characterisation platform of claim 11, wherein the particle characterisation platform is configured to flow a sample to the sample measurer to perform the first measurement, then to the particle separator to separate the sample, and then back to the sample measurer to perform the second measurement.

15. The particle characterisation platform of claim 11, wherein the sample measurer is a first sample measurer, and the particle characterisation platform comprises a second sample measurer; wherein the particle characterisation platform is configured to flow a sample to the first sample measurer to perform the first measurement, then to the particle separator to separate the sample, and then to the second sample measurer to perform the second measurement.

16. The particle characterisation platform of claim 11, wherein the first measurement comprises UV photometry and light scattering.

17. The particle characterisation platform of claim 11, wherein the second measurement comprises UV photometry and light scattering.

18. The particle characterisation platform of claim 11, wherein the instrument is configured to provide a quantitative analysis of the proportions of the sample in all the following categories:
i) monomer, corresponding with the size of relative molecular weight of a particle of interest;
ii) particles with lower size or molecular weight than the monomer;
iii) oligomers of the monomer, or particles with size or molecular weight higher than the monomer, up a particle size or molecular weight that is excluded from the second measurement; and
iv) large aggregates, comprising particles that are excluded from the second measurement.

* * * * *